(12) United States Patent
Park et al.

(10) Patent No.: US 11,414,690 B1
(45) Date of Patent: Aug. 16, 2022

(54) URIDINE DIPHOSPHATE GLYCOSYLTRANSFERASE AND USE THEREOF

(71) Applicant: CJ CHEILJEDANG CORPORATION, Seoul (KR)

(72) Inventors: Sunghee Park, Seoul (KR); Jungeun Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 17/650,591

(22) Filed: Feb. 10, 2022

(30) Foreign Application Priority Data

Oct. 19, 2021 (KR) .................. 10-2021-0139474

(51) Int. Cl.
*C12P 19/56* (2006.01)
*C12N 9/10* (2006.01)
*C12N 1/20* (2006.01)
*A23L 27/30* (2016.01)
*C12N 15/70* (2006.01)

(52) U.S. Cl.
CPC .............. *C12P 19/56* (2013.01); *A23L 27/33* (2016.08); *C12N 1/20* (2013.01); *C12N 9/1051* (2013.01); *C12N 15/70* (2013.01); *C12Y 204/01017* (2013.01); *A23V 2002/00* (2013.01); *C12N 2800/101* (2013.01)

(58) Field of Classification Search
CPC ...................................... C12P 19/56
See application file for complete search history.

(56) References Cited

FOREIGN PATENT DOCUMENTS

KR 10-1404728 6/2014

*Primary Examiner* — Suzanne M Noakes
(74) *Attorney, Agent, or Firm* — Knobbbe Martens Olson & Bear LLP

(57) ABSTRACT

A novel uridine diphosphate (UDP)-glycosyltransferase B (UGT-B), a polynucleotide encoding the uridine diphosphate (UDP)-glycosyltransferase B (UGT-B), an expression vector containing the polynucleotide, a microorganism comprising the uridine diphosphate (UDP)-glycosyltransferase B (UGT-B) or a polynucleotide encoding the uridine diphosphate (UDP)-glycosyltransferase B (UGT-B), and a method for producing rebaudioside D and rebaudioside M using the microorganism.

15 Claims, 3 Drawing Sheets
Specification includes a Sequence Listing.

[Fig. 1]
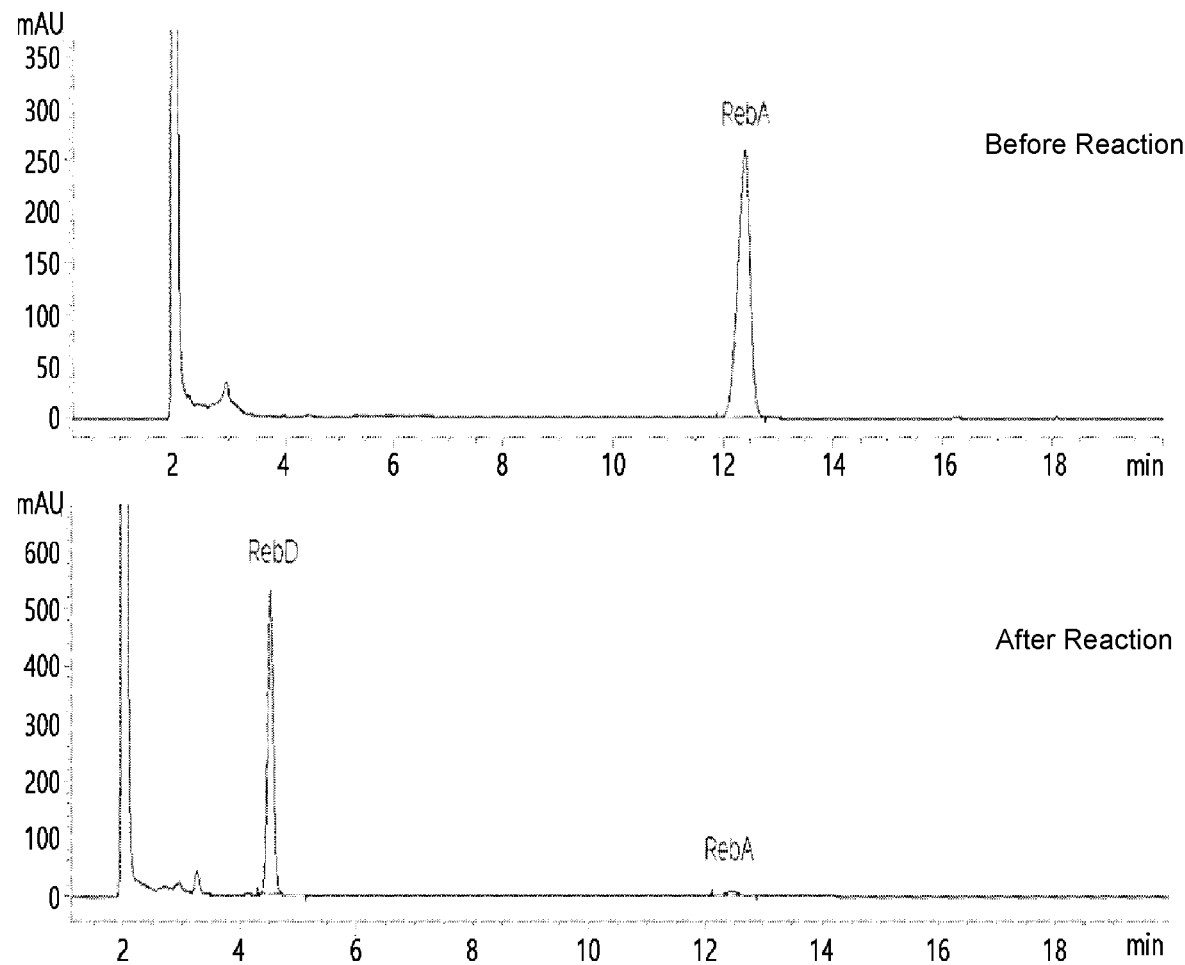

[Fig. 2]
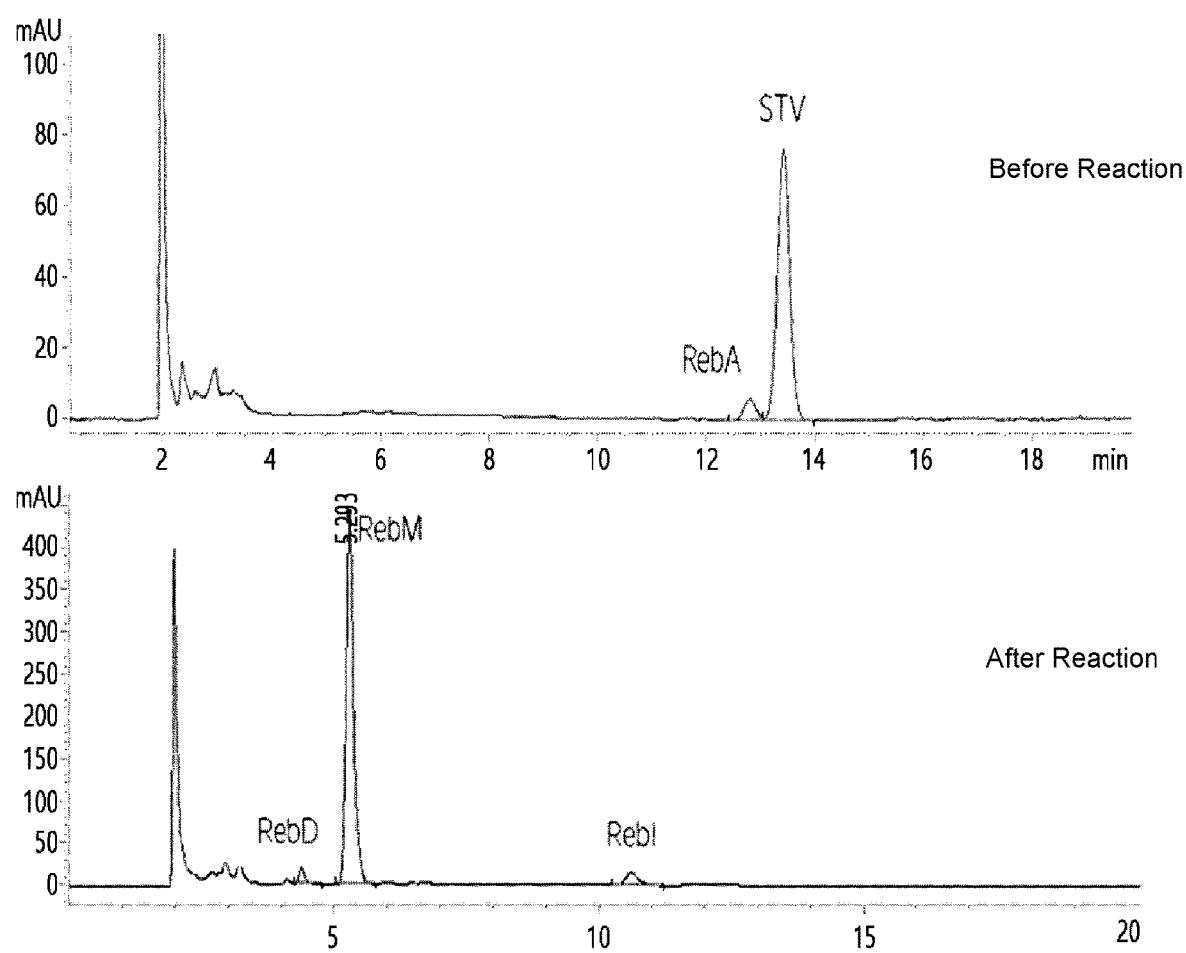

[Fig. 3]
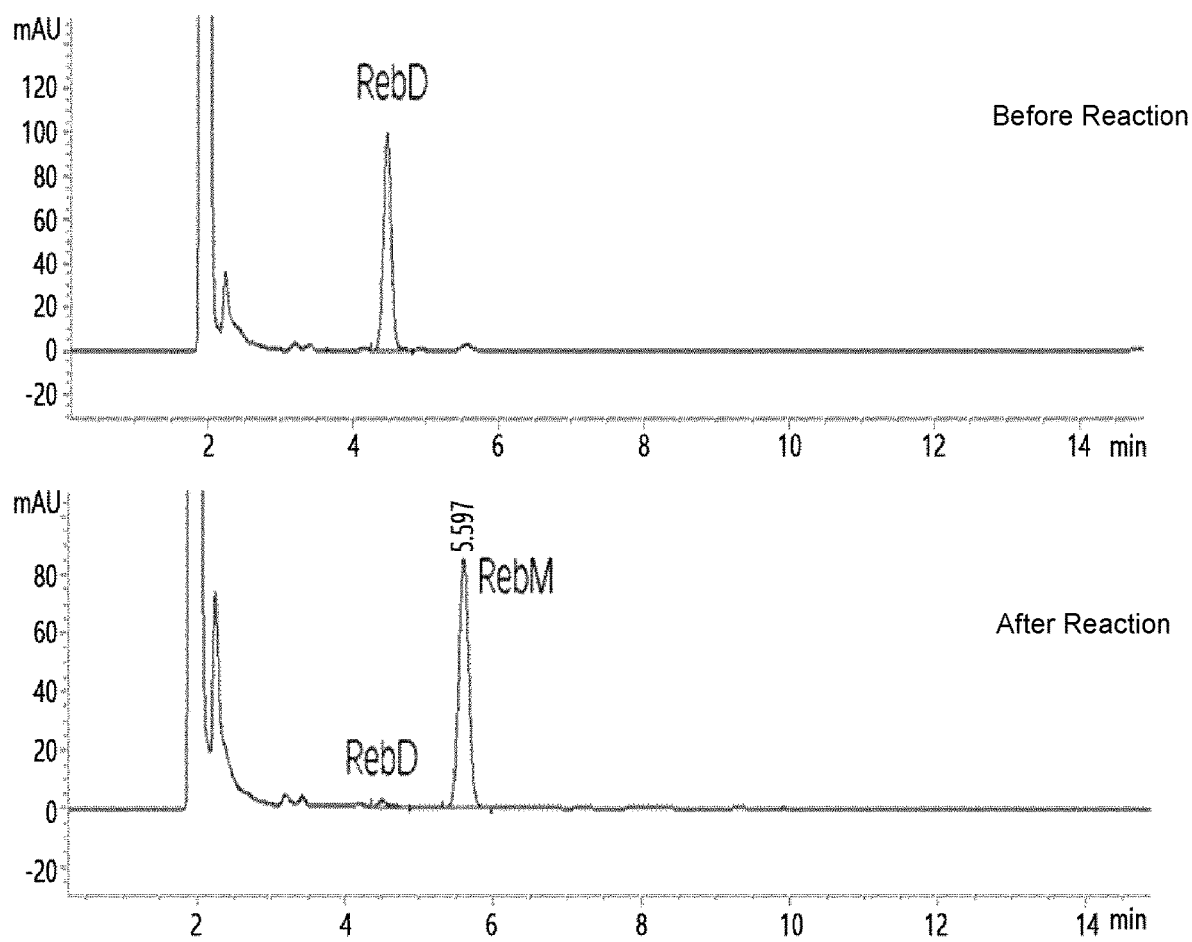

SEQUENCE LISTING

<160> NUMBER OF SEQ ID NOS: 6

<210> SEQ ID NO 1
<211> LENGTH: 463
<212> TYPE: PRT

<213> ORGANISM: Unknown
<220> FEATURE:
<223> OTHER INFORMATION: UGT-B

<400> SEQUENCE: 1

```
Met Asp Gly Asp Gly Asn Ser Ser Ser Ser Pro Leu His Val
1               5                   10                  15

Val Ile Cys Pro Trp Leu Ala Leu Gly His Leu Leu Pro Cys Leu Asp
                20                  25                  30

Ile Ala Glu Arg Leu Ala Ser Arg Gly His Arg Val Ser Phe Val Ser
            35                  40                  45

Thr Pro Arg Asn Ile Ala Arg Leu Pro Pro Leu Arg Pro Ala Val Ala
    50                  55                  60

Pro Leu Val Glu Phe Val Ala Leu Pro Leu Pro His Val Asp Gly Leu
65                  70                  75                  80

Pro Glu Gly Ala Glu Ser Thr Asn Asp Val Pro Tyr Asp Lys Phe Glu
                85                  90                  95

Leu His Arg Lys Ala Phe Asp Gly Leu Ala Ala Pro Phe Ser Glu Phe
            100                 105                 110

Leu Arg Ala Ala Cys Ala Glu Gly Ala Gly Ser Arg Pro Asp Trp Leu
        115                 120                 125

Ile Val Asp Thr Phe His His Trp Ala Ala Ala Ala Val Glu Asn
    130                 135                 140

Lys Val Pro Cys Val Met Leu Leu Leu Gly Ala Ala Thr Val Ile Ala
145                 150                 155                 160

Gly Phe Ala Arg Gly Val Ser Glu His Ala Ala Ala Val Gly Lys
                165                 170                 175

Glu Arg Pro Ala Ala Glu Ala Pro Ser Phe Glu Thr Glu Arg Arg Lys
            180                 185                 190

Leu Met Thr Thr Gln Asn Ala Ser Gly Met Thr Val Ala Glu Arg Tyr
        195                 200                 205

Phe Leu Thr Leu Met Arg Ser Asp Leu Val Ala Ile Arg Ser Cys Ala
    210                 215                 220

Glu Trp Glu Pro Glu Ser Val Ala Ala Leu Thr Thr Leu Ala Gly Lys
225                 230                 235                 240

Pro Val Val Pro Leu Gly Leu Leu Pro Pro Ser Pro Glu Gly Gly Arg
                245                 250                 255

Gly Val Ser Lys Glu Asp Ala Thr Val Arg Trp Leu Asp Ala Gln Pro
            260                 265                 270

Thr Lys Ser Val Val Tyr Val Ala Leu Gly Ser Glu Val Pro Leu Gly
        275                 280                 285

Ala Lys Glu Val His Glu Leu Ala Leu Gly Leu Glu Leu Ala Gly Thr
    290                 295                 300

Arg Phe Leu Trp Ser Leu Arg Lys Pro Ser Gly Val Ser Asp Ala Asp
305                 310                 315                 320

Ile Leu Pro Ser Gly Phe Glu Glu Arg Thr Arg Gly Arg Gly Leu Val
                325                 330                 335

Thr Met Gly Trp Val Pro Gln Ile Ser Val Leu Ala His Gly Ala Val
            340                 345                 350

Gly Ala Phe Leu Thr His Cys Gly Trp Asn Ser Ile Ile Glu Gly Leu
        355                 360                 365

Gln Phe Gly His Pro Leu Val Met Leu Pro Ile Phe Gly Asp Gln Gly
    370                 375                 380

Pro Asn Ala Arg Met Met Glu Gly Arg Lys Val Gly Val Gln Val Pro
```

```
                385                 390                 395                 400
Arg Asp Glu Ser Asn Gly Ser Phe Asp Arg Glu Gly Val Ala Thr Thr
                    405                 410                 415

Val Arg Ala Val Ala Val Glu Glu Gly Asn Arg Ile Phe Thr Ala
                420                 425                 430

Asn Ala Lys Lys Met Gln Glu Ile Val Ala Asp Lys Gly Cys His Asp
                435                 440                 445

Lys Tyr Val Asp Lys Phe Ile Gln Lys Leu Arg Ser Tyr Met Glu
            450                 455                 460

<210> SEQ ID NO 2
<211> LENGTH: 458
<212> TYPE: PRT
<213> ORGANISM: Unknown
<220> FEATURE:
<223> OTHER INFORMATION: UGT-A

<400> SEQUENCE: 2

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
```

```
            290                 295                 300
Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 3
<211> LENGTH: 808
<212> TYPE: PRT
<213> ORGANISM: Unknown
<220> FEATURE:
<223> OTHER INFORMATION: Sucrose synthase

<400> SEQUENCE: 3

Met Ala Ala Lys Leu Ala Arg Leu His Ser Leu Arg Glu Arg Leu Gly
1               5                   10                  15

Ala Thr Phe Ser Ser His Pro Asn Glu Leu Ile Ala Leu Phe Ser Arg
                20                  25                  30

Tyr Val Asn Gln Gly Lys Gly Met Leu Gln Arg His Gln Leu Leu Ala
            35                  40                  45

Glu Phe Asp Ala Leu Ile Glu Ala Asp Lys Glu Lys Tyr Ala Pro Phe
        50                  55                  60

Glu Asp Ile Leu Arg Ala Ala Gln Gly Ala Ile Val Leu Pro Pro Trp
65                  70                  75                  80

Val Ala Leu Ala Ile Arg Pro Arg Pro Gly Val Trp Asp Tyr Ile Arg
                85                  90                  95

Val Asn Val Ser Glu Leu Ala Val Glu Glu Leu Ser Val Ser Glu Tyr
            100                 105                 110

Leu Ala Phe Lys Glu Gln Leu Val Asp Gly His Thr Asn Ser Asn Phe
        115                 120                 125

Val Leu Glu Leu Asp Phe Glu Pro Phe Asn Ala Ser Phe Pro Arg Pro
    130                 135                 140

Ser Met Ser Lys Ser Ile Gly Asn Gly Val Gln Phe Leu Asn Arg His
145                 150                 155                 160

Leu Ser Ser Lys Leu Phe Gln Asp Lys Glu Ser Leu Tyr Pro Leu Leu
                165                 170                 175

Asn Phe Leu Lys Ala His Asn His Lys Gly Thr Thr Met Met Leu Asn
            180                 185                 190

Asp Arg Ile Gln Ser Leu Arg Gly Leu Gln Ser Ser Leu Arg Lys Ala
```

```
            195                 200                 205
Glu Glu Tyr Leu Met Gly Ile Pro Gln Asp Thr Pro Tyr Ser Glu Phe
        210                 215                 220

Asn His Arg Phe Gln Glu Leu Gly Leu Glu Lys Gly Trp Gly Asp Cys
225                 230                 235                 240

Ala Lys Arg Val Leu Asp Thr Ile His Leu Leu Asp Leu Leu Glu
                245                 250                 255

Ala Pro Asp Pro Ala Asn Leu Glu Lys Phe Leu Gly Thr Ile Pro Met
                260                 265                 270

Met Phe Asn Val Val Ile Leu Ser Pro His Gly Tyr Phe Ala Gln Ser
            275                 280                 285

Asn Val Leu Gly Tyr Pro Asp Thr Gly Gly Gln Val Val Tyr Ile Leu
        290                 295                 300

Asp Gln Val Arg Ala Leu Glu Asn Glu Met Leu Leu Arg Ile Lys Gln
305                 310                 315                 320

Gln Gly Leu Asp Ile Thr Pro Lys Ile Leu Ile Val Thr Arg Leu Leu
                325                 330                 335

Pro Asp Ala Val Gly Thr Thr Cys Gly Gln Arg Val Glu Lys Val Ile
                340                 345                 350

Gly Thr Glu His Thr Asp Ile Leu Arg Val Pro Phe Arg Ser Glu Asn
            355                 360                 365

Gly Ile Leu Arg Lys Trp Ile Ser Arg Phe Asp Val Trp Pro Phe Leu
        370                 375                 380

Glu Thr Tyr Thr Glu Asp Val Ala Asn Glu Ile Met Arg Glu Met Gln
385                 390                 395                 400

Ala Lys Pro Asp Leu Ile Ile Gly Asn Tyr Ser Asp Gly Asn Leu Val
                405                 410                 415

Ala Thr Leu Leu Ala His Lys Leu Gly Val Thr Gln Cys Thr Ile Ala
                420                 425                 430

His Ala Leu Glu Lys Thr Lys Tyr Pro Asn Ser Asp Ile Tyr Leu Asp
            435                 440                 445

Lys Phe Asp Ser Gln Tyr His Phe Ser Cys Gln Phe Thr Ala Asp Leu
        450                 455                 460

Ile Ala Met Asn His Thr Asp Phe Ile Ile Thr Ser Thr Phe Gln Glu
465                 470                 475                 480

Ile Ala Gly Ser Lys Asp Thr Val Gly Gln Tyr Glu Ser His Ile Ala
                485                 490                 495

Phe Thr Leu Pro Gly Leu Tyr Arg Val Val His Gly Ile Asp Val Phe
                500                 505                 510

Asp Pro Lys Phe Asn Ile Val Ser Pro Gly Ala Asp Met Ser Val Tyr
            515                 520                 525

Phe Pro Tyr Thr Glu Ala Asp Lys Arg Leu Thr Ala Phe His Pro Glu
        530                 535                 540

Ile Glu Glu Leu Leu Tyr Ser Glu Val Glu Asn Asp Glu His Lys Phe
545                 550                 555                 560

Val Leu Lys Asp Lys Asn Lys Pro Ile Ile Phe Ser Met Ala Arg Leu
                565                 570                 575

Asp Arg Val Lys Asn Met Thr Gly Leu Val Glu Met Tyr Gly Lys Asn
                580                 585                 590

Ala His Leu Arg Asp Leu Ala Asn Leu Val Ile Val Cys Gly Asp His
            595                 600                 605

Gly Asn Gln Ser Lys Asp Arg Glu Glu Gln Ala Glu Phe Lys Lys Met
        610                 615                 620
```

-continued

Tyr Gly Leu Ile Asp Gln Tyr Lys Leu Lys Gly His Ile Arg Trp Ile
625                 630                 635                 640

Ser Ala Gln Met Asn Arg Val Arg Asn Gly Glu Leu Tyr Arg Tyr Ile
                645                 650                 655

Cys Asp Thr Lys Gly Val Phe Val Gln Pro Ala Phe Tyr Glu Ala Phe
                660                 665                 670

Gly Leu Thr Val Ile Glu Ala Met Thr Cys Gly Leu Pro Thr Ile Ala
            675                 680                 685

Thr Cys His Gly Gly Pro Ala Glu Ile Ile Val Asp Gly Val Ser Gly
690                 695                 700

Leu His Ile Asp Pro Tyr His Ser Asp Lys Ala Ala Asp Ile Leu Val
705                 710                 715                 720

Asn Phe Phe Glu Lys Cys Lys Gln Asp Ser Thr Tyr Trp Asp Asn Ile
                725                 730                 735

Ser Gln Gly Gly Leu Gln Arg Ile Tyr Glu Lys Tyr Thr Trp Lys Leu
            740                 745                 750

Tyr Ser Glu Arg Leu Met Thr Leu Thr Gly Val Tyr Gly Phe Trp Lys
        755                 760                 765

Tyr Val Ser Asn Leu Glu Arg Arg Glu Thr Arg Arg Tyr Ile Glu Met
770                 775                 780

Phe Tyr Ala Leu Lys Tyr Arg Ser Leu Ala Ser Ala Val Pro Leu Ala
785                 790                 795                 800

Val Asp Gly Glu Ser Thr Ser Lys
            805

<210> SEQ ID NO 4
<211> LENGTH: 1392
<212> TYPE: DNA
<213> ORGANISM: Unknown
<220> FEATURE:
<223> OTHER INFORMATION: UGT-B

<400> SEQUENCE: 4
atggatggtg acggcaactc ctccagttcg agtagtccgc tgcatgtagt tatatgcccg      60
tggttagcct tgggccattt actgccgtgt ctggatattg ccgaacgcct ggcgagccgc     120
ggccaccgtg tctcatttgt ctccacgccg cgcaacatcg cgcgcttgcc gccgctgcgc     180
cccgctgtgg cgccgctcgt cgaatttgtc gccctgcctc taccgcatgt cgatggtttg     240
cctgaaggcg cagaaagtac aaacgatgtc ccatacgaca aattcgagtt acatcgcaaa     300
gcctttgatg gcctcgctgc acccttttca gagtttctgc gtgcagcttg tgccgagggc     360
gctggatctc ggcccgattg gcttatagtg gataccttcc accactgggc agccgcggct     420
gccgtcgaaa ataaagttcc gtgcgttatg cttttgctgg gagctgcgac agtgatcgca     480
ggtttcgctc gaggtgtgtc tgagcacgcc gctgcagccg tcgggaaaga gcgaccggca     540
gcggaagcgc atctttttga gactgaaagg aggaagctga tgaccacgca gaatgcaagc     600
gggatgacgg tagccgaacg ctacttctta acgttaatgc gtagcgatct cgtggccatt     660
cggagctgtg ctgagtggga gccagagagc gtcgccgcgt taaccacctt agcgggcaag     720
ccagtcgtcc ctttgggttt gctaccaccg tcgcccgaag gaggtcgcgg tgtgagcaag     780
gaggatgcaa ccgtgcgttg gctcgatgcc agccgaccaa atcagtggt ttatgtcgcg     840
ctaggctcgg aagtcccact gggagccaag gaagtacatg aacttgcctt aggccttgag     900
ttagcaggga cacgcttcct ttggtctctg cgcaaacctt ctggcgtaag tgatgcagac     960

```
atcctcccctt cgggttttga agagcggacc cgcggccgtg gtcttgtgac gatgggctgg      1020
gttcctcaga ttagcgtact ggcacacggt gcagtaggtg cattcctgac tcattgtgga      1080
tggaactcta tcatagaggg gttacaattt gggcatcctt tagtgatgtt gcctatcttt      1140
ggtgaccaag gtcccaatgc gcgtatgatg gaggggagaa aagttggagt gcaggtgcca      1200
agagatgaat ccaatggaag tttcgacaga gaaggcgtcg ctacaaccgt tcgggcggtc      1260
gctgtcgagg aagaaggtaa tagaattttc actgctaatg ccaaaaaaat gcaagagatc      1320
gttgcggaca aggatgccca tgacaagtat gtcgataaat ttattcagaa actgagatct      1380
tatatggagt ga                                                          1392

<210> SEQ ID NO 5
<211> LENGTH: 1377
<212> TYPE: DNA
<213> ORGANISM: Unknown
<220> FEATURE:
<223> OTHER INFORMATION: UGT-A

<400> SEQUENCE: 5
atggaaaata aaacggagac caccgttcgc cggcgccgga gaataatatt attcccggta        60
ccatttcaag gccacattaa cccaattctt cagctagcca atgtgttgta ctctaaagga       120
ttcagtatca ccatctttca caccaacttc aacaaaccca aacatctaa ttaccctcac        180 ttcactttca gattcatcct cgacaacgac ccacaagacg aacgcatttc caatctaccg       240
actcatggtc cgctcgctgg tatgcggatt ccgattatca acgaacacgg agctgacgaa       300
ttacgacgcg aactggaact gttgatgtta gcttctgaag aagatgaaga ggtatcgtgt       360
ttaatcacgg atgctctttg gtacttcgcg caatctgttg ctgacagtct taacctccga       420
cggcttgttt tgatgacaag cagcttgttt aattttcatg cacatgtttc acttcctcag       480
tttgatgagc ttggttacct cgatcctgat gacaaaaccc gtttggaaga caagcgagt        540 gggtttccta tgctaaaagt gaaagacatc aagtctgcgt attcgaactg gcaaatactc       600
aaagagatat tagggaagat gataaaacaa acaaaagcat cttcaggagt catctggaac       660
tcatttaagg aactcgaaga gtctgagctc gaaactgtta tccgtgagat cccggctcca       720
agtttcttga taccactccc caagcatttg acagcctctt ccagcagctt actagaccac       780
gatcgaaccg tttttcaatg gttagaccaa caaccgccaa gttcggtact gtatgttagt       840
tttggtagta ctagtgaagt ggatgagaaa gatttcttgg aaatagctcg tgggttggtt       900
gatagcaagc agtcgttttt atgggtggtt cgacctgggg ttgtcaaggg ttcgacgtgg       960
gtcgaaccgt tgccagatgg gttcttgggt gaaagaggac gtattgtgaa atgggttcca      1020
cagcaagaag tgctagctca tggagcaata ggcgcattct ggactcatag cggatggaac      1080
tctacgttgg aaagcgtttg tgaaggtgtt cctatgattt tctcggattt tgggctcgat      1140
caaccgttga atgctagata catgagtgat gttttgaagg tagggtgta tttgaaaat       1200 gggtgggaaa gaggagagat agcaaatgca ataagaagag ttatggtgga tgaagaagga      1260
gaatacatta gacagaatgc aagagttttg aaacaaaagg cagatgtttc tttgatgaag      1320
ggtggttcgt cttacgaatc attagagtct ctagtttctt acatttcatc gttgtaa         1377

<210> SEQ ID NO 6
<211> LENGTH: 2427
<212> TYPE: DNA
<213> ORGANISM: Unknown
<220> FEATURE:
<223> OTHER INFORMATION: Sucrose synthase
```

<400> SEQUENCE: 6

```
atggctgcca agctagctcg cctccacagt ctccgcgaac gcctcggtgc caccttctcg      60
tctcatccca atgagttgat tgcactcttc tctaggtatg ttaaccaggg aaagggaatg     120
ctccagcgtc accagctgct tgcggagttc gatgccttga tcgaagctga caagagaaa     180
tatgctccct ttgaagacat tctccgggct gctcaggaag ccattgtgct gccgccctgg     240
gttgcactgg ccatcaggcc aaggcctggt gtctgggact acattcgggt gaatgtaagt     300
gagttggcag tggaagagct gagtgtttct gagtacttgg cattcaagga acagcttgtt     360
gatggacaca ccaacagcaa ctttgttctt gagcttgatt ttgagccctt caatgcctcc     420
ttcccgcgcc cgtccatgtc caagtccatc ggaaatgggg tgcagttcct taaccgtcac     480
ctgtcgtcca agttgttcca ggacaaggag agcctctacc ccttgctgaa cttcctgaaa     540
gcccataacc acaagggcac gacaatgatg ctgaatgaca gaattcagag ccttcgtggg     600
ctccaatcat cccttagaaa ggcagaagaa tatctgatgg gcattcctca agacacgccc     660
tactcggagt tcaaccacag gttccaagag ctcggtttgg agaagggttg gggtgactgt     720
gcaaagcgtg tgcttgacac catccacttg cttcttgacc ttcttgaggc ccctgatccg     780
gccaacttgg agaagttcct tggaactatt ccaatgatgt tcaatgttgt tatcctgtct     840
ccgcatggat actttgccca atccaatgtg ttgggatacc ctgatactgg tggtcaggtt     900
gtgtacattt tggaccaagt ccgcgctttg gagaatgaga tgcttttgag gatcaagcag     960
caaggccttg atatcacacc taagatcctc attgtaacca ggctgttgcc tgatgctgtt    1020
ggtactacat gcggccagcg tgtggagaag gttattggaa ctgagcacac tgacattctt    1080
cgtgttccat tcaggagtga aatggtatc ctccgcaagt ggatctcccg ttttgatgtc    1140
tggccattcc tggaaacata cactgaggat gttgcaaacg aaattatgag ggaaatgcaa    1200
gccaaacctg atctcatcat tggcaattac agtgatggaa ccttgttgc cactctgctg    1260
gctcacaaat taggagttac ccagtgtacc attgctcatg ccttggagaa aaccaaatac    1320
cccaactcag acatatactt ggacaagttt gacagccagt accacttctc atgccaattc    1380
actgctgatc ttatcgccat gaatcacact gatttcatca tcaccagtac attccaagaa    1440
attgctggaa gcaaggacac tgtggggcag tatgaatcac acattgcatt caccccttcct    1500
gggctttacc gagttgtgca tggcatagat gttttttgatc ccaagttcaa cattgtctct    1560
cctggagctg acatgagtgt ctacttcccg tacaccgagg ctgacaagag gctcactgct    1620
ttccacccct aaaattgagga gcttctctac agtgaagtcg agaacgatga acacaagttt    1680
gtattgaagg acaagaacaa gccaatcatc ttctccatgg ctcgtcttga ccgagtgaag    1740
aacatgacag gtctggttga gatgtatggt aagaatgcac atctcaggga tttggcaaac    1800
cttgtgattg tttgtggtga ccacggcaat cagtccaagg acagggagga gcaggctgag    1860
ttcaagaaga tgtacggtct cattgaccag tacaagttga aggggcatat ccgctggatc    1920
tcagctcaga tgaaccgtgt tcgtaacggg gagttgtacc gatacatttg tgacaccaag    1980
ggagtctttg tccagcctgc attctatgaa gcgtttggtc tgactgtcat cgaagccatg    2040
acatgtggtt tgccaacaat cgcaacatgc catggtggcc ctgctgagat tattgttgat    2100
ggggtgtctg gtctgcacat tgatccttac cacagtgaca aggctgctga tatcttggtc    2160
aacttctttg agaagtgcaa gcaggattca acctactggg acaatatttc acagggaggt    2220
ctgcagagga tttacgagaa gtacacctgg aagctgtact ctgagaggct gatgaccttg    2280
```

-continued

```
actggtgtat acggattctg gaagtacgta agcaaccttg agaggcgcga gactcgccgt    2340
tacattgaga tgttctatgc tctgaaatac cgcagcctgg ccagcgccgt cccattggct    2400
gtcgatggag agagcacatc caagtaa                                        2427
```

URIDINE DIPHOSPHATE GLYCOSYLTRANSFERASE AND USE THEREOF

RELATED APPLICATION

This application claims priority to Korean Patent Application No. 10-2021-0139474, filed Oct. 19, 2021, the entire content of which is incorporated herein by reference.

SEQUENCE LISTING STATEMENT

The present application contains a Sequence Listing, which is being submitted via EFS-Web on even date herewith. The Sequence Listing is submitted in a file entitled "Sequence_Listing.txt", which was created on Feb. 9, 2022, and is approximately 21 kb in size. This Sequence Listing is incorporated by reference.

TECHNICAL FIELD

The present application relates to a novel uridine diphosphate (UDP)-glycosyltransferase B (UGT-B), a polynucleotide encoding the uridine diphosphate (UDP)-glycosyltransferase B (UGT-B), an expression vector containing the polynucleotide, a microorganism including the uridine diphosphate (UDP)-glycosyltransferase B (UGT-B) or a polynucleotide encoding the uridine diphosphate (UDP)-glycosyltransferase B (UGT-B), and a method for producing rebaudioside D and rebaudioside M using the microorganism.

BACKGROUND ART

As the World Health Organization (WHO) recommends lowering the amount of daily sugar intake due to concerns about disease (obesity) caused by sugar consumption, various policies aimed at reducing the amount of sugar intake are actively being discussed by the governments of developed countries. Therefore, as the need for developing various alternative sweeteners in place of sugar and high-fructose sweeteners is increasing in the market, alternative sweeteners are continuously being developed and commercialized.

Such alternative sweeteners are the subject of continuous variation in the form of synthetic high-intensity sweeteners (e.g., saccharin, aspartame, sucralose, etc.), synthetic sugar alcohols (e.g., maltitol and xylitol), and high-intensity sweeteners (e.g., rebaudioside A and liquorice). Nevertheless, due to concerns over the safety of synthetic sweeteners, customers' need for natural sweeteners has been steadily increasing; however, because of limitations with peculiar flavor properties of natural sweeteners (i.e., off-odor and off-flavor), natural sweeteners cannot fully replace existing low-calorie and zero-calorie products based on synthetic sweeteners.

A natural high-intensity sweetener that has received considerable attention in recent years is stevia extracted from the leaves of Stevia. Stevia has a potential use as an alternative sweetener because it has been reported that it does not generate calories, it is positive for blood glucose and insulin levels, and has no side effects on the human body; however, stevia has a limitation in use for reducing the amount of sugar because it has a bitter taste.

Stevia is a perennial plant in the Asteraceae family native to Paraguay in South America, and its scientific name is Stevia rebaudiana Bertoni. The leaves of Stevia contain sweetening components which have 200 to 300 times the sweetness of sugar, and the sweetening components are extracted and used as a natural sweetener. The sweetening components of the Stevia extracts contain various steviol glycosides such as stevioside, rebaudioside A, rebaudioside C, rebaudioside D, rebaudioside M, rebaudioside I, rebaudioside E, etc.

The Stevia leaves contain relatively high contents of stevioside (STV), rebaudioside A (Reb A), and rebaudioside C (Reb C) among the sweetening components of the Stevia extract, and thus, high-purity extracted and purified industrial products have been launched, but they have a limitation in use for reducing the amount of sugar because of bitter taste.

Meanwhile, rebaudioside D (Reb D) and rebaudioside M (Reb M) have less bitter taste than STV, rebaudioside A, and rebaudioside C, and have excellent sweetening qualities, and thus are highly valuable as alternative sweeteners.

However, rebaudioside D and rebaudioside M are present only in very small amounts in the Stevia leaves, so there is a disadvantage in that a method of extracting and purifying rebaudioside D and rebaudioside M from the leaves and producing the same requires a high cost.

Accordingly, there is a need for research on novel enzymes required for mass production of rebaudioside D and rebaudioside M and a production method using the same.

PRIOR ART LITERATURE

Patent Literature (Patent Literature 0001) Korean Patent No. 1404728

Technical Problem

The present inventors have made extensive efforts to develop an enzyme having an activity to convert rebaudioside A to rebaudioside D, and as a result, it has been newly found that a polypeptide sequence whose function was not previously revealed has a glycosyltransferase activity, and that the polypeptide has a glycosyltransferase activity of converting rebaudioside A into rebaudioside D, thereby completing the present application.

Technical Solution

One object of the present application is to provide uridine diphosphate (UDP)-glycosyltransferase B (UGT-B) consisting of an amino acid sequence of SEQ ID NO: 1.

Another object of the present application is to provide a polynucleotide encoding the uridine diphosphate (UDP)-glycosyltransferase B (UGT-B) consisting of an amino acid sequence of SEQ ID NO: 1.

Still another object of the present application is to provide an expression vector containing a polynucleotide encoding uridine diphosphate (UDP)-glycosyltransferase B (UGT-B) consisting of an amino acid sequence of SEQ ID NO: 1.

Yet another object of the present application is to provide a microorganism comprising uridine diphosphate (UDP)-glycosyltransferase B (UGT-B) consisting of an amino acid sequence of SEQ ID NO: 1 or a polynucleotide encoding the uridine diphosphate (UDP)-glycosyltransferase B (UGT-B).

Even another object of the present application is to provide a method for producing rebaudioside D, comprising: reacting nucleotide diphosphate to which glucose is bonded with rebaudioside A in the presence of uridine diphosphate (UDP)-glycosyltransferase B (UGT-B) to prepare rebaudioside D, wherein the uridine diphosphate (UDP)-glycosyltransferase B (UGT-B) is a protein consisting of an amino acid sequence of SEQ ID NO: 1.

In a method for producing rebaudioside D according to any one of the previous specific embodiments, the nucleotide diphosphate to which glucose is bonded is prepared by reacting sucrose and nucleotide diphosphate in the presence of a sucrose synthase.

In a method for producing rebaudioside D according to any one of the previous specific embodiments, the rebaudioside A is prepared by reacting nucleotide diphosphate to which glucose is bonded with stevioside in the presence of uridine diphosphate (UDP)-glycosyltransferase A (UGT-A).

In a method for producing rebaudioside D according to any one of the previous specific embodiments, the sucrose synthase is a protein consisting of an amino acid sequence of SEQ ID NO: 3.

In a method for producing rebaudioside D according to any one of the previous specific embodiments, the uridine diphosphate (UDP)-glycosyltransferase A (UGT-A) is a protein consisting of an amino acid sequence of SEQ ID NO: 2.

In a method for producing rebaudioside D according to any one of the previous specific embodiments, the method for producing rebaudioside D is performed consecutively in situ.

Further another object of the present application is to provide a method for producing rebaudioside M, comprising: reacting nucleotide diphosphate to which glucose is bonded with rebaudioside A in the presence of uridine diphosphate (UDP)-glycosyltransferase B (UGT-B) to prepare rebaudioside D; and reacting the rebaudioside D with nucleotide diphosphate to which glucose is bonded in the presence of uridine diphosphate (UDP)-glycosyltransferase A (UGT-A) to prepare rebaudioside M, wherein the uridine diphosphate (UDP)-glycosyltransferase B (UGT-B) is a protein consisting of an amino acid sequence of SEQ ID NO: 1.

In a method for producing rebaudioside M according to any one of the previous specific embodiments, the uridine diphosphate (UDP)-glycosyltransferase A (UGT-A) is a protein consisting of an amino acid sequence of SEQ ID NO: 2.

In a method for producing rebaudioside M according to any one of the previous specific embodiments, the nucleotide diphosphate to which glucose is bonded is prepared by reacting sucrose with nucleotide diphosphate in the presence of a sucrose synthase.

In a method for producing rebaudioside M according to any one of the previous specific embodiments, the rebaudioside A is prepared by reacting nucleotide diphosphate to which glucose is bonded with stevioside in the presence of uridine diphosphate (UDP)-glycosyltransferase A (UGT-A).

In a method for producing rebaudioside M according to any one of the previous specific embodiments, the sucrose synthase is a protein consisting of an amino acid sequence of SEQ ID NO: 3.

In a method for producing rebaudioside M according to any one of the previous specific embodiments, the uridine diphosphate (UDP)-glycosyltransferase A (UGT-A) is a protein consisting of an amino acid sequence of SEQ ID NO: 2.

In a method for producing rebaudioside M according to any one of the previous specific embodiments, the method for producing rebaudioside M is performed consecutively in situ.

Still further another object of the present application is to provide a method for producing rebaudioside D from rebaudioside A, comprising: reacting sucrose, nucleotide diphosphate, rebaudioside A, sucrose synthase and uridine diphosphate (UDP)-glycosyltransferase B (UGT-B) in situ to prepare rebaudioside D, wherein the uridine diphosphate (UDP)-glycosyltransferase B (UGT-B) is a protein consisting of an amino acid sequence of SEQ ID NO: 1.

Still further another object of the present application is to provide a method for producing rebaudioside M from rebaudioside A, comprising: reacting sucrose, nucleotide diphosphate, rebaudioside A, rebaudioside D, sucrose synthase, uridine diphosphate (UDP)-glycosyltransferase A (UGT-A) and uridine diphosphate (UDP)-glycosyltransferase B (UGT-B) in situ to prepare rebaudioside M, wherein the uridine diphosphate (UDP)-glycosyltransferase B (UGT-B) is a protein consisting of an amino acid sequence of SEQ ID NO: 1.

In a method for producing rebaudioside M from rebaudioside A according to any one of the previous specific embodiments, the uridine diphosphate (UDP)-glycosyltransferase A (UGT-A) is a protein consisting of an amino acid sequence of SEQ ID NO: 2.

Still further another object of the present application is to provide a composition for producing rebaudioside D including the uridine diphosphate (UDP)-glycosyltransferase B (UGT-B).

Still further another object of the present application is to provide a composition for producing rebaudioside M including the uridine diphosphate (UDP)-glycosyltransferase A (UGT-A).

Still further another object of the present application is to provide the use of uridine diphosphate (UDP)-glycosyltransferase B (UGT-B) consisting of an amino acid sequence of SEQ ID NO: 1 as a glycosyltransferase that converts rebaudioside A to rebaudioside D.

Advantageous Effects

The uridine diphosphate (UDP)-glycosyltransferase B (UGT-B) of the present application can be used to produce rebaudioside D and/or rebaudioside M, thereby providing rebaudioside D and rebaudioside M in high purity and high yield, with almost no by-products, and thus can be effectively used for mass production of rebaudioside D and rebaudioside M because it is economical due to the use of inexpensive raw materials, and the procedure is simple and less time-consuming.

BRIEF DESCRIPTION OF THE DRAWINGS

FIG. 1 is a HPLC analysis result showing that rebaudioside A is converted to rebaudioside D by uridine diphosphate (UDP)-glycosyltransferase B (UGT-B).

FIG. 2 is a HPLC analysis result showing that rebaudioside D, rebaudioside M, and rebaudioside I are produced from stevioside and rebaudioside A by uridine diphosphate (UDP)-glycosyltransferase B (UGT-B), uridine diphosphate (UDP)-glycosyltransferase A (UGT-A), and sucrose synthase.

FIG. 3 is a HPLC analysis result showing that rebaudioside D is converted to rebaudioside M by uridine diphosphate (UDP)-glycosyltransferase A (UGT-A).

DETAILED DESCRIPTION OF PREFERRED EMBODIMENTS

The present application will be described in detail as follows. Meanwhile, each description and embodiment disclosed herein can be applied to other descriptions and embodiments, respectively. That is, all combinations of various elements disclosed herein fall within the scope of the present application. Further, the scope of the present application is not limited by the specific description described below. Additionally, a number of papers and patent documents have been cited throughout the present specification. The content of the cited papers and patent documents is incorporated herein by reference in their entirety and the level of technical field to which the present application belongs and the contents of the present application will be described more clearly.

One aspect of the present application provides uridine diphosphate (UDP)-glycosyltransferase B (UGT-B) consisting of an amino acid sequence of SEQ ID NO: 1.

As used herein, the term "uridine diphosphate (UDP)-glycosyltransferase (UGT)" is an enzyme that catalyzes the transfer of a monosaccharide moiety from a glycosyl donor to a glycosyl acceptor molecule, and in particular, it refers to an enzyme that utilizes UDP-sugar as the glycosyl donor. In the present application, the UDP-glycosyltransferase may be interchangeably used with UGT.

The UDP-glycosyltransferase may be one produced from recombinant *E. coli*, *Bacillus*, yeast, *Corynebacterium* or *Agrobacterium* transformed with a vector containing a glycosyltransferase gene, and the UDP-glycosyltransferase may be further purified after production from *E. coli* or the like, or commercially manufactured products may be purchased and used, but the UDP-glycosyltransferase is not limited thereto. In addition, the UDP-glycosyltransferase is known in the art, and the protein and gene sequence of the UDP-glycosyltransferase can be obtained from a known database, for example, GenBank of NCBI, etc., but is not limited thereto.

In the present application, the novel uridine diphosphate (UDP)-glycosyltransferase B (UGT-B) consisting of an amino acid sequence of SEQ ID NO: 1 having an enzyme activity of converting rebaudioside A to rebaudioside D has been newly discovered.

Specifically, the uridine diphosphate (UDP)-glycosyltransferase B (UGT-B) of the present application may have and/or include an amino acid sequence of SEQ ID NO: 1 or essentially consist or consist of the amino acid sequence.

Additionally, the uridine diphosphate (UDP)-glycosyltransferase B (UGT-B) may include an amino acid sequence having a homology or identity of at least 70%, 75%, 80%, 85%, 90%, 95%, 96%, 97%, 98%, 99%, 99.5%, 99.7%, or 99.9% or more with the amino acid sequence of SEQ ID NO: 1. In addition, it is apparent that any uridine diphosphate (UDP)-glycosyltransferase B (UGT-B) having an amino acid sequence, in which part of the sequence is deleted, modified, substituted, conservatively substituted, or added, may also fall within the scope of the present application as long as the amino acid sequence has such a homology or identity and exhibits an effect corresponding to that of the uridine diphosphate (UDP)-glycosyltransferase B (UGT-B).

As used herein, although it is described as "a polypeptide or protein including an amino acid sequence described by a specific sequence number", "a polypeptide or protein consisting of an amino acid sequence described by a specific sequence number", or "a polypeptide or protein having an amino acid sequence described by a specific sequence number", it is apparent that any protein having an amino acid sequence in which part of the sequence is deleted, modified, substituted, conservatively substituted or added can be used in the present application even if it has the same or corresponding activity as the polypeptide consisting of the amino acid sequence of the corresponding sequence number. For example, it may be a case where the N-terminus and/or C-terminus of the amino acid sequence is added with a sequence that does not alter the function of the protein, a naturally occurring mutation, a potential mutation thereof (a silent mutation), or a conservative substitution.

For example, it may be a case where the N-terminus, C-terminus and/or inside of the amino acid sequence is added or deleted with a sequence that does not alter the function of the uridine diphosphate (UDP)-glycosyltransferase B (UGT-B) of the present application, a naturally occurring mutation, a potential mutation thereof (a silent mutation), or a conservative substitution.

As used herein, the term "conservative substitution" refers to substitution of an amino acid with another amino acid having similar structural and/or chemical properties. Such amino acid substitution may generally occur based on similarity of polarity, charge, solubility, hydrophobicity, hydrophilicity, and/or amphipathic nature of a residue. For example, positively charged (basic) amino acids include arginine, lysine, and histidine; negatively charged (acidic) amino acids include glutamic acid and aspartic acid; aromatic amino acids include phenylalanine, tryptophan, and tyrosine; and hydrophobic amino acids include alanine, valine, isoleucine, leucine, methionine, phenylalanine, tyrosine, and tryptophan. In addition, amino acids can be classified into amino acids with electrically charged side chains and amino acids with uncharged side chains, and examples of the amino acids with electrically charged side chains include aspartic acid, glutamic acid, lysine, arginine, and histidine. The amino acids with uncharged side chains can be further classified into nonpolar amino acids or polar amino acids. Examples of the non-polar amino acids are glycine, alanine, valine, leucine, isoleucine, methionine, phenylalanine, tryptophan, proline, and examples of the polar amino acids include serine, threonine, cysteine, tyrosine, asparagine, and glutamine. Typically, conservative substitutions have little or no effect on the activity of the resulting polypeptide. Typically, conservative substitutions may have little or no effect on the activity of the protein or polypeptide.

Additionally, the uridine diphosphate (UDP)-glycosyltransferase B (UGT-B) may also include deletion or addition of amino acids that have minimal influence on the properties and secondary structure of a polypeptide. For example, the polypeptide may be conjugated with a signal (or leader) sequence at the N-terminal involved in the transfer of proteins co-translationally or post-translationally. Further, the polypeptide may also be conjugated with another sequence or linker to identify, purify, or synthesize the polypeptide.

As used herein, the term "homology" or "identity" refers to a degree of relatedness between two given amino acid sequences or nucleotide sequences, and may be expressed as a percentage. The terms homology and identity may often be used interchangeably with each other.

The sequence homology or identity of conserved polynucleotide or polypeptide sequences may be determined by standard alignment algorithms and can be used with a default gap penalty established by the program being used. Substantially, homologous or identical sequences are generally expected to hybridize to all or part of the sequences under moderate or high stringent conditions. It is apparent that hybridization with polynucleotides containing general codon or degenerate codons in hybridizing polynucleotides is also included.

Whether any two polynucleotide or polypeptide sequences have a homology, similarity, or identity may be, for example, determined by a known computer algorithm such as the "FASTA" program (Pearson et al., (1988) *Proc.*

*Natl. Acad. Sci. USA* 85:2444) using default parameters. Alternatively, it may be determined by the Needleman-Wunsch algorithm (Needleman and Wunsch, 1970, *J. Mol. Biol.* 48:443-453), which is performed using the Needleman program of the EMBOSS package (EMBOSS: The European Molecular Biology Open Software Suite, Rice et al., 2000, *Trends Genet.* 16:276-277) (preferably, version 5.0.0 or later) (GCG program package (Devereux, J. et al., *Nucleic Acids Research* 12:387 (1984)), BLASTP, BLASTN, FASTA (Atschul, S. F. et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity, or identity may be determined using BLAST or ClustalW of the National Center for Biotechnology Information (NCBI).

The homology, similarity, or identity of polynucleotides or polypeptides may be, for example, determined by comparing sequence information using, for example, the GAP computer program, such as Needleman et al. (1970), *J Mol Biol.* 48:443 as disclosed in Smith and Waterman, *Adv. Appl. Math* (1981) 2:482. In summary, the GAP program defines the homology, similarity, or identity as the value obtained by dividing the number of similarly aligned symbols (i.e., nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358 (1979) (or EDNAFULL substitution matrix (EMBOSS version of NCBI NUC4.4)); (2) a penalty of 3.0 for each gap and an additional 0.10 penalty for each symbol in each gap (or a gap opening penalty of 10 and a gap extension penalty of 0.5); and (3) no penalty for end gaps.

In one example of the present application, the uridine diphosphate (UDP)-glycosyltransferase B (UGT-B) may have an activity of converting rebaudioside A to rebaudioside M.

As used herein, the term "corresponding to" refers to an amino acid residue at the position recited in a peptide, or an amino acid residue which is similar, identical, or homologous to the residue recited in a peptide. Identifying an amino acid at a corresponding position may be determining a particular amino acid in a sequence that refers to a particular sequence. As used herein, the "corresponding region" generally refers to a similar or corresponding position in the related protein or reference protein.

For example, any amino acid sequence is aligned with SEQ ID NO: 1, and based on the alignment, each amino acid residue of the amino acid sequence can be numbered with reference to the numerical position of the amino acid residue corresponding to the amino acid residue of SEQ ID NO: 1. For example, a sequence alignment algorithm such as that described herein can identify the position of an amino acid or a position where modifications such as substitutions, insertions or deletions occur compared to a query sequence (also referred to as a "reference sequence").

Example of the alignment may be determined using the Needleman-Wunsch algorithm (Needleman and Wunsch, 1970, *J. Mol. Biol.* 48:443-453), which is performed using the Needleman program of the EMBOSS package (EMBOSS: The European Molecular Biology Open Software Suite, Rice et al., 2000, *Trends Genet.* 16:276-277), etc., but is not limited thereto, and sequence alignment programs, such as pairwise sequence comparison algorithms, etc., known in the art may be appropriately used.

Another aspect of the present application provides a polynucleotide encoding the uridine diphosphate (UDP)-glycosyltransferase B (UGT-B) of the present application.

As used herein, the term "polynucleotide", which is a polymer of nucleotides composed of nucleotide monomers connected in a lengthy chain by a covalently bond, is a DNA or RNA strand having at least a certain length. More specifically, it may refer to a polynucleotide fragment encoding the uridine diphosphate (UDP)-glycosyltransferase B (UGT-B).

The polynucleotide encoding the uridine diphosphate (UDP)-glycosyltransferase B (UGT-B) of the present application may include a nucleotide sequence encoding the amino acid sequence represented by SEQ ID NO: 1. As an example of the present application, the polynucleotide may have or include the sequence of SEQ ID NO: 4. In addition, the polynucleotide may consist or consist essentially of the sequence of SEQ ID NO: 4.

The polynucleotide of the present application may undergo various modifications in the coding region within the scope that does not change the amino acid sequence of the uridine diphosphate (UDP)-glycosyltransferase B (UGT-B) of the present application, due to codon degeneracy or in consideration of the codons preferred in an organism in which the uridine diphosphate (UDP)-glycosyltransferase B (UGT-B) of the present application is to be expressed. Specifically, the polynucleotide of the present application may have or include a nucleotide sequence having a homology or identity of 70% or more, 75% or more, 80% or more, 85% or more, 90% or more, 95% or more, 96% or more, 97% or more, 98% or more, and 100% or less with the sequence of SEQ ID NO: 4, or may consist or consist essentially of a nucleotide sequence having a homology or identity of 70% or more, 75% or more, 80% or more, 85% or more, 90% or more, 95% or more, 96% or more, 97% or more, 98% or more, and 100% or less with the sequence of SEQ ID NO: 4, but is not limited thereto.

Additionally, the polynucleotide of the present application may include a probe that may be prepared from a known gene sequence, for example, any sequence which can hybridize with a sequence complementary to all or part of the polynucleotide sequence of the present application under stringent conditions without limitation. The "stringent conditions" refers to conditions under which specific hybridization between polynucleotides is allowed. Such conditions are specifically described in the literature (J. Sambrook et al., Molecular Cloning, *A Laboratory Manual*, 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York, 9.50-9.51, 11.7-11.8). For example, the stringent conditions may include conditions under which genes having a high homology or identity of 70% or more, 75% or more, 80% or more, 85% or more, 90% or more, 95% or more, 96% or more, 97% or more, 98% or more, or 99% or more are hybridized with each other and genes having a homology or identity lower than the above homologies or identities are not hybridized with each other, or washing conditions of Southern hybridization, that is, washing once, specifically twice or three times at a salt concentration and a temperature corresponding to 60° C., 1×SSC, 0.1% SDS, specifically 60° C., 0.1×SSC, 0.1% SDS, and more specifically 68° C., 0.1×SSC, 0.1% SDS.

Hybridization requires that two nucleic acids contain complementary sequences, although mismatches between bases are possible depending on the stringency of the hybridization. The term "complementary" is used to describe the relationship between nucleotide bases that can hybridize with each other. For example, with respect to DNA, adenine is complementary to thymine, and cytosine is complementary to guanine. Therefore, the polynucleotide of the present application may include isolated nucleotide fragments complementary to the entire sequence as well as nucleic acid sequences substantially similar thereto.

Specifically, polynucleotides having a homology or identity with the polynucleotide of the present application may be detected using the hybridization conditions including a hybridization step at a $T_m$ value of 55° C. under the above-described conditions. Further, the $T_m$ value may be 60° C., 63° C., or 65° C., but is not limited thereto, and may be appropriately adjusted by those skilled in the art depending on the purpose thereof.

The appropriate stringency for hybridizing the polynucleotides depends on the length of the polynucleotides and the degree of complementation, and these variables are well known in the art (e.g., Sambrook et al.).

Still another aspect of the present application provides a vector containing the polynucleotide of the present application. The vector may be an expression vector for expressing the polynucleotide in a microorganism, but is not limited thereto.

As used herein, the term "vector" may include a DNA construct containing the nucleotide sequence of a polynucleotide encoding the target polypeptide operably linked to a suitable expression regulatory region (expression regulatory sequence) so as to be able to express the target polypeptide in a suitable host cell. The expression regulatory sequence may include a promoter capable of initiating transcription, any operator sequence for regulating the transcription, a sequence encoding a suitable mRNA ribosome-binding site, and a sequence for regulating termination of transcription and translation. Once transformed into a suitable microorganism, the vector may replicate or function independently from the host genome, or may integrate into genome thereof.

The vector used in the present application is not particularly limited, and any vector known in the art may be used. Examples of the vector typically used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, and Charon21A, etc. may be used; and as a plasmid vector, those based on pDZ, pBR, pUC, pBluescriptII, pGEM, pTZ, pCL and pET, etc. may be used. Specifically, pDZ, pDC, pDCM2, pACYC177, pACYC184, pCL, pECCG117, pUC19, pBR322, pMW118, pCC1 BAC vector, etc. may be used.

In one example, a polynucleotide encoding a target polypeptide may be inserted into the chromosome through a vector for intracellular chromosomal insertion. The insertion of the polynucleotide into the chromosome may be performed by any method known in the art, for example, by homologous recombination, but is not limited thereto. The vector may further include a selection marker to confirm the insertion into the chromosome. The selection marker is for selecting the cells transformed with the vector, that is, for confirming whether the target nucleic acid molecule has been inserted, and markers that provide selectable phenotypes, such as drug resistance, auxotrophy, resistance to cell toxic agents, or expression of surface polypeptides, may be used. Only cells expressing the selection marker are able to survive or to show different phenotypes under the environment treated with the selective agent, and thus the transformed cells may be selected.

As used herein, the term "transformation" refers to the introduction of a vector containing a polynucleotide encoding a target polypeptide into a microorganism so that the polypeptide encoded by the polynucleotide can be expressed in the microorganism. As long as the transformed polynucleotide can be expressed in the microorganism, it does not matter whether the transformed polynucleotide is integrated into the chromosome of the microorganism and located therein or located extrachromosomally, and both cases can be included. Further, the polynucleotide may include DNA and/or RNA encoding the target polypeptide. The polynucleotide may be introduced in any form, as long as it can be introduced into the microorganism and expressed therein. For example, the polynucleotide may be introduced into the microorganism in the form of an expression cassette, which is a gene construct including all elements required for its autonomous expression. The expression cassette may commonly include a promoter operably linked to the polynucleotide, a transcription terminator, a ribosome-binding site, or a translation terminator. The expression cassette may be in the form of a self-replicable expression vector. Additionally, the polynucleotide may be introduced into a microorganism as it is and operably linked to sequences required for expression in the microorganism, but is not limited thereto.

Further, as used herein, the term "operably linked" means that the polynucleotide sequence is functionally linked to a promoter sequence that initiates and mediates transcription of the polynucleotide encoding the target uridine diphosphate (UDP)-glycosyltransferase B (UGT-B) of the present application.

Yet another aspect of the present application provides a microorganism including the uridine diphosphate (UDP)-glycosyltransferase B (UGT-B) of the present application or a polynucleotide encoding the uridine diphosphate (UDP)-glycosyltransferase B (UGT-B).

The microorganism of the present application may include the uridine diphosphate (UDP)-glycosyltransferase B (UGT-B) of the present application, a polynucleotide encoding the uridine diphosphate (UDP)-glycosyltransferase B (UGT-B), or a vector containing the polynucleotide of the present application.

As used herein, the term "microorganism" includes all wild-type microorganisms, or naturally or artificially genetically modified microorganisms, and it may be a microorganism in which a particular mechanism is weakened or enhanced due to insertion of a foreign gene, or enhancement or inactivation of the activity of an endogenous gene, and may be a microorganism including genetic modification to produce a desired polypeptide, protein or product. In the present application, the terms "microorganism" and "strain" have the same meaning and can be used interchangeably without limitation.

Specifically, the microorganism may be a microorganism of the genus *Escherichia* or a microorganism of the genus *Corynebacterium*, more specifically *Escherichia coli* or *Corynebacterium glutamicum*, but is not limited thereto.

The microorganism of the present application may be a strain including any one or more of the uridine diphosphate (UDP)-glycosyltransferase B (UGT-B) of the present application, the polynucleotide of the present application, and a vector containing the polynucleotide of the present application; a strain modified to express the uridine diphosphate (UDP)-glycosyltransferase B (UGT-B) of the present application or the polynucleotide of the present application; a strain expressing the uridine diphosphate (UDP)-glycosyltransferase B (UGT-B) of the present application or the polynucleotide of the present application (e.g., a recombinant strain); or a strain having the activity of the uridine diphosphate (UDP)-glycosyltransferase B (UGT-B) of the present application (e.g., a recombinant strain), but is not limited thereto.

The strain of the present application may be a microorganism producing rebaudioside D and/or rebaudioside M.

As used herein, the term "microorganism producing rebaudioside D and/or rebaudioside M" refers to a prokaryotic or eukaryotic microorganism strain capable of producing rebaudioside D and/or rebaudioside M in an organism. For the purpose of the present invention, as long as the microorganism can produce rebaudioside D and/or rebaudioside M including the uridine diphosphate (UDP)-glycosyltransferase B (UGT-B), both prokaryotic and eukaryotic cells are possible.

The microorganism producing rebaudioside D and/or rebaudioside M including the uridine diphosphate (UDP)-glycosyltransferase B (UGT-B) may include all microorganisms including the uridine diphosphate (UDP)-glycosyltransferase B (UGT-B) by introducing a microorganism including the sequence encoding the uridine diphosphate (UDP)-glycosyltransferase B (UGT-B) on the chromosome and/or a vector including a polynucleotide encoding the uridine diphosphate (UDP)-glycosyltransferase B (UGT-B), but is not limited thereto.

In one example, the strain of the present application is a cell or microorganism which is transformed with a vector containing the polynucleotide of the present application or a polynucleotide encoding the uridine diphosphate (UDP)-glycosyltransferase B (UGT-B) of the present application to express the uridine diphosphate (UDP)-glycosyltransferase B (UGT-B) of the present application, and for the purpose of the present application, the strain may include all microorganisms capable of producing rebaudioside D and/or rebaudioside M including the uridine diphosphate (UDP)-glycosyltransferase B (UGT-B) of the present application. For example, the strain of the present application may be a recombinant strain in which the production ability of rebaudioside D and/or rebaudioside M has been increased upon expression of the uridine diphosphate (UDP)-glycosyltransferase B (UGT-B) by introducing the polynucleotide encoding the uridine diphosphate (UDP)-glycosyltransferase B (UGT-B) of the present application into a natural wild-type microorganism or a microorganism for producing rebaudioside D and/or rebaudioside M.

The modification of a part or all of the polynucleotide in the microorganism of the present application may be achieved by (a) homologous recombination using a vector for chromosomal insertion in the microorganism or genome editing using engineered nuclease (e.g., CRISPR-Cas9) and/or (b) may be induced by light, such as ultraviolet rays and radiation, etc., and/or chemical treatments, but is not limited thereto. The method of modifying a part or all of the gene may include a method using DNA recombination technology. For example, a part or all of the gene may be deleted by injecting a nucleotide sequence or a vector containing a nucleotide sequence homologous to the target gene into the microorganism to induce homologous recombination. The injected nucleotide sequence or the vector may include a dominant selection marker, but is not limited thereto.

In the microorganism of the present application, the uridine diphosphate (UDP)-glycosyltransferase B (UGT-B), polynucleotide and rebaudioside D and/or rebaudioside M, etc., are as described in other aspects.

Even another aspect of the present application provides a method for producing rebaudioside D, including:

reacting nucleotide diphosphate to which glucose is bonded with rebaudioside A in the presence of uridine diphosphate (UDP)-glycosyltransferase B (UGT-B) to prepare rebaudioside D, wherein the uridine diphosphate (UDP)-glycosyltransferase B (UGT-B) is a protein consisting of an amino acid sequence of SEQ ID NO: 1.

Specifically, the method for producing rebaudioside D of the present application may include culturing a microorganism including the uridine diphosphate (UDP)-glycosyltransferase B (UGT-B) of the present application, the polynucleotide of the present application, or the vector of the present application in a medium, but is not limited thereto.

As used herein, the term "cultivation" means that the microorganism of the present application is grown under appropriately controlled environmental conditions. The cultivation process of the present application may be performed in a suitable culture medium and culture conditions known in the art. Such a cultivation process may be easily adjusted for use by those skilled in the art according to the strain to be selected. Specifically, the cultivation may be a batch culture, a continuous culture, and/or a fed-batch culture, but is not limited thereto.

As used herein, the term "medium" refers to a mixture of materials which contains nutrient materials required for the cultivation of the microorganism of the present application as a main ingredient, and it supplies nutrient materials and growth factors, along with water that is essential for survival and growth. Specifically, the medium and other culture conditions used for culturing the microorganism of the present application may be any medium used for conventional cultivation of microorganisms without any particular limitation. However, the microorganism of the present application may be cultured under aerobic conditions in a conventional medium containing an appropriate carbon source, nitrogen source, phosphorus source, inorganic compounds, amino acids, and/or vitamins, while adjusting temperature, pH, etc.

For example, the culture medium for the microorganism of the genus *Corynebacterium* can be found in the literature ("Manual of Methods for General Bacteriology" by the American Society for Bacteriology (Washington D.C., USA, 1981)).

In the present application, the carbon source may include carbohydrates, such as glucose, saccharose, lactose, fructose, sucrose, maltose, etc.; sugar alcohols, such as mannitol, sorbitol, etc.; organic acids, such as pyruvic acid, lactic acid, citric acid, etc.; amino acids, such as glutamic acid, methionine, lysine, etc. Additionally, the carbon source may include natural organic nutrients such as starch hydrolysate, molasses, blackstrap molasses, rice bran, cassava, sugar cane molasses, corn steep liquor, etc. Specifically, carbohydrates such as glucose and sterilized pretreated molasses (i.e., molasses converted to reducing sugar) may be used, and in addition, various other carbon sources in an appropriate amount may be used without limitation. These carbon sources may be used alone or in a combination of two or more kinds, but are not limited thereto.

The nitrogen source may include inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources, such as peptone, NZ-amine, meat extract, yeast extract, malt extract, corn steep liquor, casein hydrolysate, fish or a decomposition product thereof, defatted soybean cake or a decomposition product thereof, etc. These nitrogen sources may be used alone or in a combination of two or more kinds, but are not limited thereto.

The phosphorus source may include monopotassium phosphate, dipotassium phosphate, or corresponding sodium-containing salts, etc. Examples of the inorganic compound may include sodium chloride, calcium chloride, iron chloride, magnesium sulfate, iron sulfate, manganese sulfate, calcium carbonate, etc. Additionally, amino acids, vitamins, and/or appropriate precursors may be included. These constituting ingredients or precursors may be added to a medium in a batch or continuous manner, but these phosphorus sources are not limited thereto.

The pH of a medium may be adjusted during the cultivation of the microorganism of the present application by adding a compound such as ammonium hydroxide, potassium hydroxide, ammonia, phosphoric acid, sulfuric acid, etc. to the medium in an appropriate manner. Additionally, during the cultivation, an antifoaming agent such as fatty acid polyglycol ester may be added to prevent foam generation. In addition, oxygen or oxygen-containing gas may be injected into the medium in order to maintain an aerobic state of the medium; or nitrogen, hydrogen, or carbon dioxide gas may be injected without the injection of gas in order to maintain an anaerobic or microaerobic state of the medium, but the gas is not limited thereto.

The medium temperature in the cultivation of the present application may be in a range from 20° C. to 45° C., and specifically from 25° C. to 40° C., and the cultivation may be carried out for about 10 to 160 hours, but is not limited thereto.

The rebaudioside D produced by the cultivation of the present application may be released into the medium or remain in the cells.

In one embodiment of the present application, the nucleotide diphosphate to which glucose is bonded may be prepared by reacting sucrose and nucleotide diphosphate in the presence of a sucrose synthase, but is not limited thereto.

As used herein, the term "sucrose synthase" has a role in the production of sucrose by reversibly transferring glucose, which is bonded to nucleotide diphosphate, to fructose in plant metabolism. In the present invention, the sucrose synthase demonstrates an activity to separate nucleotide diphosphate to which glucose is bonded and fructose by reacting sucrose and nucleotide diphosphate in a pH range of 5 to 10.

The sucrose synthase may be those derived from rice, corn, wheat, bamboo, *Arabidopsis thaliana*, grass, barley, sorghum or potato. Preferably, the sucrose synthase is those derived from rice, corn, wheat, or barley, and more preferably from rice, in particular, *Oryza sativa*. The sucrose synthase may be produced from recombinant *Escherichia coli, Bacillus*, yeast, *Corynebacterium*, or *Agrobacterium* transformed with a vector containing a sucrose synthase gene, and may be further purified after it is produced from *Escherichia coli* and the like. The sucrose synthase may be those known in the art or may be commercially purchased, but is not limited thereto.

Specifically, the sucrose synthase of the present application may have and/or include an amino acid sequence of SEQ ID NO: 3 or may consist or essentially consist of the amino acid sequence.

The sucrose is not particularly limited so long as it can serve as a substrate for sucrose synthase to provide glucose to nucleotide diphosphate. Examples of sucrose may include raw sugar or sugar without limitation.

In the present application, purine nucleotide or pyrimidine nucleotide may be used as the nucleotide diphosphate. Preferably, uridine diphosphate is used as the nucleotide diphosphate, but the nucleotide diphosphate is not limited thereto.

The nucleotide diphosphate to which glucose is bonded may be reacted with rebaudioside A to prepare rebaudioside D by the uridine diphosphate (UDP)-glycosyltransferase B (UGT-B) of the present application.

In one embodiment of the present application, the rebaudioside A may be prepared by reacting nucleotide diphosphate to which glucose is bonded with stevioside in the presence of uridine diphosphate (UDP)-glycosyltransferase A (UGT-A), but is not limited thereto.

The uridine diphosphate (UDP)-glycosyltransferase A (UGT-A) may produce rebaudioside A by reacting the nucleotide diphosphate to which glucose is bonded with stevioside.

The uridine diphosphate (UDP)-glycosyltransferase A (UGT-A) may be those derived from *Oryza sativa, Stevia rebaudiana Bertoni, Bambusa oldhamii, Brachypodium distachyon, Hordeum vulgare, Sorghum bicolor, Zea mays*, or *Arabidopsis thaliana*. Preferably, the uridine diphosphate (UDP)-glycosyltransferase A (UGT-A) may be those derived from *Oryza sativa, Stevia rebaudiana Bertoni*, or *Bambusa oldhamii*. More preferably, it may be those derived from *Stevia rebaudiana Bertoni*. The uridine diphosphate (UDP)-glycosyltransferase A (UGT-A) may be those produced from recombinant *Escherichia coli, Bacillus*, yeast, *Corynebacterium* or *Agrobacterium* transformed with a vector containing a glycosyltransferase gene, or may be further purified after it is produced from *Escherichia coli* and the like. The uridine diphosphate (UDP)-glycosyltransferase A (UGT-A) may be those known in the art or may be commercially purchased, but is not limited thereto.

Specifically, the uridine diphosphate (UDP)-glycosyltransferase A (UGT-A) of the present application may have and/or include an amino acid sequence of SEQ ID NO: 2 or may consist or essentially consist of the amino acid sequence.

The stevioside is a hot water or aqueous ethanol solution extract from *Stevia rebaudiana* or purified material thereof, or a by-product after the production of rebaudioside A from the extract. The stevioside may be those having stevioside content of 10 wt % or more, preferably 50 wt % or more, particularly preferably 70 wt % or more, and more particularly preferably 80 wt % or more, based on total weight of steviol glycoside, but is not limited thereto.

In one embodiment of the present application, the rebaudioside D may be produced as illustrated in the Chemical Reaction 1 below, but is not limited thereto.

[Chemical Reaction 1]

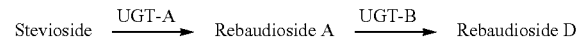

Specifically, the production method may be performed consecutively in situ.

As used herein, the term "in situ" means that a reaction is consecutively performed in a single reaction system.

The production method of the present application provides a consecutive reaction system, wherein one glucose is specifically bonded to the C-3' position of stevioside 13-O-glucose to synthesize rebaudioside A with high yield, and rebaudioside D is synthesized from rebaudioside A in accordance with the Chemical Reaction 1 above.

The method for producing rebaudioside D of the present application may further include a step of preparing the microorganism of the present application, a step of preparing a medium for culturing the strain, or a combination thereof (regardless of the order, in any order), for example, prior to the culturing step.

The method for producing rebaudioside D of the present application may further include a step of recovering rebaudioside D from the culture medium (medium on which the culture was grown) or the microorganism of the present application. The recovering step may be further included after the culturing step.

In the recovering step, desired rebaudioside D may be collected using the method of culturing a microorganism of the present application, for example, using a suitable method known in the art according to a batch culture, continuous culture, or fed-batch culture method. For example, methods such as centrifugation, filtration, treatment with a protein crystallizing precipitant (salting-out method), extraction, ultrasonic disruption, ultrafiltration, dialysis, various kinds of chromatography such as molecular sieve chromatography (gel filtration), adsorption chromatography, ion-exchange chromatography, affinity chromatography, etc., HPLC, or a combination thereof may be used, and the desired rebaudioside D can be recovered from the medium or the microorganisms using suitable methods known in the art.

Further, the method for producing rebaudioside D of the present application may further include a purification process, which may be performed using an appropriate method known in the art. In one example, when the method for producing rebaudioside D of the present application includes both a recovering step and a purification step, the recovering step and the purification step may be performed continuously or intermittently regardless of the order or simultaneously, or may be integrated into one step, but the method is not limited thereto.

In the method of the present application, the uridine diphosphate (UDP)-glycosyltransferase B (UGT-B), polynucleotides, vectors and microorganism, etc. are the same as described in other aspects.

Further aspect of the present application provides a method for producing rebaudioside M, including:

reacting nucleotide diphosphate to which glucose is bonded with rebaudioside A in the presence of uridine diphosphate (UDP)-glycosyltransferase B (UGT-B) to prepare rebaudioside D; and reacting the rebaudioside D with nucleotide diphosphate to which glucose is bonded in the presence of uridine diphosphate (UDP)-glycosyltransferase A (UGT-A) to prepare rebaudioside M, wherein the uridine diphosphate (UDP)-glycosyltransferase B (UGT-B) is a protein consisting of an amino acid sequence of SEQ ID NO: 1.

In one embodiment of the present application, the uridine diphosphate (UDP)-glycosyltransferase A (UGT-A) may be a protein consisting of an amino acid sequence of SEQ ID NO: 2, but is not limited thereto.

In one embodiment of the present application, the nucleotide diphosphate to which glucose is bonded may be prepared by reacting sucrose with nucleotide diphosphate in the presence of a sucrose synthase, but is not limited thereto.

Specifically, the sucrose synthase of the present application may have and/or include an amino acid sequence of SEQ ID NO: 3 or may consist or essentially consist of the amino acid sequence.

In one embodiment of the present application, the rebaudioside A may be prepared by reacting nucleotide diphosphate to which glucose is bonded with stevioside in the presence of uridine diphosphate (UDP)-glycosyltransferase A (UGT-A), but is not limited thereto.

Specifically, the uridine diphosphate (UDP)-glycosyltransferase A (UGT-A) of the present application may have and/or include an amino acid sequence of SEQ ID NO: 2 or may consist or essentially consist of the amino acid sequence.

The uridine diphosphate (UDP)-glycosyltransferase A (UGT-A) of the present application may produce rebaudioside M by reacting the nucleotide diphosphate to which glucose is bonded with rebaudioside D.

Specifically, the uridine diphosphate (UDP)-glycosyltransferase A (UGT-A) of the present application may have and/or include an amino acid sequence of SEQ ID NO: 2 or may consist or essentially consist of the amino acid sequence.

In one embodiment of the present application, the rebaudioside M may be produced as illustrated in the Chemical Reaction 2 below, but is not limited thereto.

[Chemical Reaction 2]

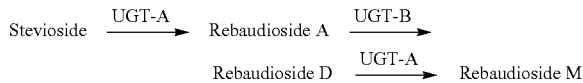

Specifically, the production method may be performed consecutively in situ.

The production method of the present application provides a consecutive reaction system, wherein rebaudioside A is synthesized from stevioside with high yield, rebaudioside D is synthesized from rebaudioside A, and rebaudioside M is synthesized from rebaudioside D, in accordance with the Chemical Reaction 2 above.

The method for producing rebaudioside M of the present application may further include a step of preparing the microorganism of the present application, a step of preparing a medium for culturing the strain, or a combination thereof (regardless of the order, in any order), for example, prior to the culturing step.

The method for producing rebaudioside M of the present application may further include a step of recovering rebaudioside M from the culture medium (medium on which the culture was grown) or the microorganism of the present application. The recovering step may be further included after the culturing step.

In the recovering step, desired rebaudioside M may be collected using the method of culturing a microorganism of the present application, for example, using a suitable method known in the art according to a batch culture, continuous culture, or fed-batch culture method. For example, methods such as centrifugation, filtration, treatment with a protein crystallizing precipitant (salting-out method), extraction, ultrasonic disruption, ultrafiltration, dialysis, various kinds of chromatographies such as molecular sieve chromatography (gel filtration), adsorption chromatography, ion exchange chromatography, affinity chromatography, etc., HPLC or a combination thereof may be used, and the desired rebaudioside M can be recovered from the medium or the microorganisms using suitable methods known in the art.

Further, the method for producing rebaudioside M of the present application may further include a purification process, which may be performed using an appropriate method known in the art. In one example, when the method for producing rebaudioside M of the present application includes both a recovering step and a purification step, the recovering step and the purification step may be performed continuously or intermittently regardless of the order or simultaneously, or may be integrated into one step, but the method is not limited thereto.

In the method of the present application, the uridine diphosphate (UDP)-glycosyltransferase B (UGT-B), polynucleotides, vectors and microorganism are the same as described in other aspects.

Accordingly, the production method of the present application uses raw materials such as stevioside and rebaudioside A, which are inexpensive and can be easily obtained, and can convert stevioside and rebaudioside A, which are components with bitter contained in *stevia* extract, into rebaudioside D and rebaudioside M, which are components with excellent taste, and thus can be effectively used in the production of *stevia* sweetener with excellent sweetening quality.

Still further another aspect of the present application provides a method for producing rebaudioside D from rebaudioside A, including:
reacting sucrose, nucleotide diphosphate, rebaudioside A, sucrose synthase and uridine diphosphate (UDP)-glycosyltransferase B (UGT-B) in situ to prepare rebaudioside D, wherein the uridine diphosphate (UDP)-glycosyltransferase B (UGT-B) is a protein consisting of an amino acid sequence of SEQ ID NO: 1.

Still further another aspect of the present application provides a method for producing rebaudioside M from rebaudioside A, including:
reacting sucrose, nucleotide diphosphate, rebaudioside A, rebaudioside D, sucrose synthase, uridine diphosphate (UDP)-glycosyltransferase A (UGT-A) and uridine diphosphate (UDP)-glycosyltransferase B (UGT-B) in situ to prepare rebaudioside M, wherein the uridine diphosphate (UDP)-glycosyltransferase B (UGT-B) is a protein consisting of an amino acid sequence of SEQ ID NO: 1.

The sucrose, nucleotide diphosphate, rebaudioside A, rebaudioside D, sucrose synthase, uridine diphosphate (UDP)-glycosyltransferase A (UGT-A), uridine diphosphate (UDP)-glycosyltransferase B (UGT-B), in situ, and rebaudioside M, etc., are the same as described in other aspects.

Specifically, the uridine diphosphate (UDP)-glycosyltransferase A (UGT-A) may be a protein consisting of an amino acid sequence of SEQ ID NO: 2, but is not limited thereto.

Still further another aspect of the present application provides a composition for producing rebaudioside D, including the uridine diphosphate (UDP)-glycosyltransferase B (UGT-B) of the present application, a polynucleotide encoding the uridine diphosphate (UDP)-glycosyltransferase B (UGT-B), a vector containing the polynucleotide, or a microorganism including the polynucleotide of the present application; a medium for culturing the microorganism; or a combination of two or more thereof.

Still further another aspect of the present application provides a composition for producing rebaudioside M, including the uridine diphosphate (UDP)-glycosyltransferase B (UGT-B) and uridine diphosphate (UDP)-glycosyltransferase A (UGT-A) of the present application, a polynucleotide encoding the uridine diphosphate (UDP)-glycosyltransferase B (UGT-B) and a polynucleotide encoding the uridine diphosphate (UDP)-glycosyltransferase A (UGT-A), a vector containing the polynucleotide, or a microorganism including the polynucleotide of the present application; a medium for culturing the microorganism; or a combination of two or more thereof.

The composition of the present application may further include any suitable excipient commonly used in the composition for producing amino acids, and such excipient may be, for example, a preservative, a wetting agent, a dispersing agent, a suspending agent, a buffering agent, a stabilizing agent, or an isotonic agent, but is not limited thereto.

In the composition of the present application, the uridine diphosphate (UDP)-glycosyltransferase B (UGT-B), uridine diphosphate (UDP)-glycosyltransferase A (UGT-A), polynucleotides, vectors, strains, media and L-valine, etc. are the same as described in the other aspects.

Still further another aspect of the present application provides the use of uridine diphosphate (UDP)-glycosyltransferase B (UGT-B) consisting of the amino acid sequence of SEQ ID NO: 1 as a glycosyltransferase that converts rebaudioside D from rebaudioside A.

The SEQ ID NO: 1, uridine diphosphate (UDP)-glycosyltransferase B (UGT-B), rebaudioside A, rebaudioside D, etc. are the same as described in other aspects.

MODE FOR CARRYING OUT THE INVENTION

Hereinafter, the present application will be described in detail by way of Examples. However, these Examples are merely preferred Examples given for illustrative purposes, and thus, the scope of the present application is not intended to be limited to or by these Examples. Meanwhile, technical features which are not described herein can be sufficiently understood and easily carried out by those skilled in the art in the technical field of the present application or in a similar technical field.

Example 1. Design of Novel Uridine Diphosphate (UDP)-Glycosyltransferase B (UGT-B)

Example 1-1. Design of Novel Uridine Diphosphate (UDP)-Glycosyltransferase B (UGT-B)

In order to develop excellent enzymes for producing rebaudioside D and rebaudioside M, two types of plant-derived enzymes, which are known to recognize *stevia* and rebaudioside A as acceptors for glycosyl transfer reaction and UDP-glucose as donors, were selected, and the expression thereof in microorganisms and their conversion activity from rebaudioside A to rebaudioside D were evaluated, and the results are shown in Table 1 below.

TABLE 1

| Wild-type protein | Origin | Protein ID | Enzyme Expression Level (--,-, +, ++) | Conversion Rate (%) (--,-, +, ++) |
|---|---|---|---|---|
| W1 | *Hordeum vulgare* | BAJ94055.1 | + | ++ |
| W2 | *Brachypodium distachyon* | XP_003560669.1 | -- | + |

As shown in Table 1, the two types of plant-derived enzymes showed a low enzyme expression level and conversion rate, which decreased the efficiency for the industrial production of rebaudioside D, and accordingly, new enzymes were designed to improve the efficiency.

Specifically, based on the chemical structure and reaction mechanism of the substrate used in the glycosyl transfer reaction of the enzymes, it could be expected that the tertiary structure of each protein belonged to the GT-B fold. Since the protein with the GT-B fold structure has a characteristic that the N-domain that recognizes the sugar acceptor is clearly distinguished from the C-domain that recognizes the sugar donor, a total of 12 types of improved enzymes were prepared, and their expressions and activities were evaluated by way of the method of mixing the N-domain and C-domain of each protein to produce a chimera.

As a result, uridine diphosphate (UDP)-glycosyltransferase B (UGT-B), a novel enzyme with smooth protein expression and improved activity in microorganisms compared to the wild-type enzyme, was prepared as shown in the schematic diagram below, and its sequence is represented by SEQ ID NO: 1.

| Schematic Diagram 1 | |
| --- | --- |
| W1 (N-domain) 256 AA | W2 (C-domain) 207 AA |

Example 1-2. Preparation of Novel Uridine Diphosphate (UDP)-Glycosyltransferase B (UGT-B) and Measurement of Activity Thereof For the novel enzyme for converting rebaudioside A to rebaudioside D designed in Example 1-1, W1 and W2 enzymes, a recombinant plasmid (vector-pET24a) containing a gene encoding UDP-glycosyltransferase was prepared and cloned into *E. coli* BL21 (DE3) to produce the enzymes on a large scale, and the enzymes were purified and used.

A test tube containing 5 mL of LB medium was inoculated with the recombinant strain BL21(DE3), followed by seed culturing in an incubator at 37° C. until the absorbance at 600 nm reached 2.0. The seed cultured-solution was added to a flask containing 500 mL of LB medium and then cultured. Further, 0.1 mM IPTG (isopropyl β-D-1-thiogalacthiopyranoside) was added until the absorbance at 600 nm reached 0.4, thereby inducing mass expression of the enzymes. The culture conditions were adjusted so that the stirring speed was 180 rpm and the culture temperature was 37° C. during the procedure, while the stirring speed was 120 rpm and the culture temperature was 16° C. after the addition of IPTG. The culture solution of the transformed strain was centrifuged at 6,000 g at 4° C. for 20 minutes to separate a cell supernatant as an enzyme solution. In order to precisely identify the properties of the enzymes, the enzyme solution was purified using a Ni-NTA superflow column.

Meanwhile, the recombinant Corynebacteria were inoculated into a medium (Bacto-Trypton 10 g/L, Bacto-yeast extract 5 g/L, NaCl 5 g/L, Soytone 5 g/L) containing kanamycin at a concentration of 10 μg/mL with an initial concentration of $O.D._{600}$=0.1, and cultured at 30° C. for 24 hours to induce expression of the enzyme. The thus-obtained culture solution was inoculated into a fermenter containing a medium (glucose 80 g/L, soytone 20 g/L, $(NH_4)_2SO_4$ 10 g/L, $KH_2PO_4$ 1.2 g/L, $MgSO_4$ 1.4 g/L) containing kanamycin at a concentration of 10 μg/mL with $O.D._{600}$=0.6 and cultured at 30° C. for 24 hours.

The raw material used in the enzymatic reaction was RebA (Daepyeong), which was dissolved in water to concentrations of 1 mM, 5 mM, 10 mM, and 20 mM, and the enzymes expressed in microorganisms (uridine diphosphate (UDP)-glycosyltransferase B (UGT-B), W1, W2) were used. The reaction was carried out at 37° C. for 24 hours and then analyzed by HPLC. UDP-glucose (Carbosynth) was added to the raw material aqueous solution at 2 mM, 10 mM, 20 mM, and 40 mM. As the enzyme, purified enzymes were used, and the reaction was carried out at an enzyme concentration of 0.1 mg/mL.

The measurement results are shown in Tables 2 and 3 below.

TABLE 2

Comparison Evaluation of Conversion Rate from Rebaudioside A to Rebaudioside D according to Substrate Concentration (%)

| Substrate Concentration (mM) | 1 mM | 5 mM | 10 mM | 20 mM |
| --- | --- | --- | --- | --- |
| W1 | 96 | 89.1 | 63.2 | 41.5 |
| W2 | 35.2 | 23.6 | 14.8 | 4.1 |
| Uridine diphosphate (UDP)-glycosyltransferase B (UGT-B) | 98.6 | 97.2 | 78.1 | 56.3 |

TABLE 3

Comparison Evaluation of Protein Expression Level

| Wild type protein | Origin | Protein ID | Enzyme Expression Level (--, -, +, ++) |
| --- | --- | --- | --- |
| W1 | *Hordeum vulgare* | BAJ94055.1 | + |
| W2 | *Brachypodium distachyon* | XP_003560669.1 | -- |
| Uridine diphosphate (UDP)-glycosyltransferase B (UGT-B) | – | – | ++ |

As shown in Tables 2 and 3, it was confirmed that the novel uridine diphosphate (UDP)-glycosyltransferase B (UGT-B) of the present application showed improved conversion yield of rebaudioside D from rebaudioside A and protein expression level.

Example 2. Measurement of Uridine Diphosphate (UDP)-Glycosyltransferase B (UGT-B) Activity for Rebaudioside a as Raw Material The enzyme activity of uridine diphosphate (UDP)-glycosyltransferase B (UGT-B) for rebaudioside A as a raw material was measured using the uridine diphosphate (UDP)-glycosyltransferase B (UGT-B) prepared in Example 1-2.

Specifically, the raw material used for the enzymatic reaction was RebA (Daepyeong), which was dissolved in water to a concentration of 2 mM, and the enzymes expressed in microorganisms (SEQ ID NO: 4) were used. The reaction was carried out at 37° C. for 16 hours and then analyzed by HPLC. The raw material aqueous solution may contain UDP-glucose or UDP (uridine-diphosphate) at a concentration of 2 mM.

The conditions for HPLC Analysis are as follows:
Detector wavelength: 210 nm
Flow rate: 1 mL/min
Sample injection vol.: 10 μL
Column: Capcell pak C18 MG II (Shiseido, 250 mm×4.6 mm, particle size: 5 μm)
Solvent: Acetonitrile 30%

The measurement results are shown in Table 4 and FIG. 1 below.

TABLE 4

| Sample | Rebaudioside D Content (%) | Rebaudioside A Content (%) |
| --- | --- | --- |
| Raw Material (Reaction Time: 0) | 0.3 | 99.7 |
| Uridine diphosphate (UDP)-glycosyltransferase B (UGT-B) | 98.6 | 1.4 |

As shown in Table 4 and FIG. 1, it was confirmed that most (98.6%) of rebaudioside A was converted to rebaudioside D by the uridine diphosphate (UDP)-glycosyltransferase B (UGT-B) of the present application.

Example 3. Measurement of Uridine Diphosphate (UDP)-Glycosyltransferase A (UGT-A) and Uridine Diphosphate (UDP)-Glycosyltransferase B (UGT-B) Activities for Stevioside as Raw Material Uridine diphosphate (UDP)-glycosyltransferase A (UGT-A) and sucrose synthase were purified using the method disclosed in the prior literature (WO 2014/133248), and their sequences were represented by SEQ ID NO: 2 and SEQ ID NO: 3, respectively.

The enzyme activities of uridine diphosphate (UDP)-glycosyltransferase B (UGT-B) and uridine diphosphate (UDP)-glycosyltransferase A (UGT-A) for stevioside as a raw material were measured using the uridine diphosphate (UDP)-glycosyltransferase A (UGT-A), sucrose synthase, and the uridine diphosphate (UDP)-glycosyltransferase B (UGT-B) prepared in Example 1-2.

Specifically, the raw material used for the enzymatic reaction were 2 mM stevioside (Haigen) and a 50 mM sugar (CJ Cheiljedang) aqueous solution, and the uridine diphosphate (UDP)-glycosyltransferase A (UGT-A), the sucrose synthase, and the uridine diphosphate (UDP)-glycosyltransferase B (UGT-B) prepared in Example 1-2, which were expressed in microorganisms, were used. The reaction was carried out at 37° C. for 16 hours and then analyzed by HPLC. The raw material aqueous solution may contain UDP-glucose or UDP (uridine-diphosphate) at a concentration of 2 mM.

The measurement results are shown in Table 5 and FIG. 2 below.

TABLE 5

| Sample | Rebaudioside D (%) | Rebaudioside M (%) | Rebaudioside I (%) | Rebaudioside A (%) | Stevioside (%) |
| --- | --- | --- | --- | --- | --- |
| Raw Material (Reaction Time: 0) | 0 | 0 | 0 | 4.6 | 95.4 |
| Uridine diphosphate (UDP)-glycosyltransferase B (UGT-B), Uridine diphosphate (UDP)-glycosyltransferase A (UGT-A), Sucrose Synthase | 3.5 | 91 | 5.5 | 0 | 0 |

As shown in Table 5 and FIG. 2, it was confirmed that 100% of stevioside and rebaudioside A was converted to rebaudioside D, rebaudioside M, and rebaudioside I relative to the molar concentration.

Example 4. Measurement of Uridine Diphosphate (UDP)-Glycosyltransferase A (UGT-A) Activity for Rebaudioside D as Raw Material The conversion rate of rebaudioside M from rebaudioside D was measured by the uridine diphosphate (UDP)-glycosyltransferase A (UGT-A) of Example 3.

Specifically, the raw material used for the enzymatic reaction was rebaudioside D (Haigen), which was dissolved in water to a concentration of 1 mM, and the uridine diphosphate (UDP)-glycosyltransferase A (UGT-A) expressed in microorganisms were used. The reaction was carried out at 37° C. for 16 hours and then analyzed by HPLC. The raw material aqueous solution may contain UDP-glucose or UDP (uridine-diphosphate) at a concentration of 2 mM.

The measurement results are shown in FIG. 3.

As shown in FIG. 3, it was confirmed that most rebaudioside D was converted to rebaudioside M by the uridine diphosphate (UDP)-glycosyltransferase A (UGT-A) of the present application.

From the foregoing, a skilled person in the art to which the present application pertains will be able to understand that the present application may be embodied in other specific forms without modifying the technical concepts or essential characteristics of the present application. In this regard, the exemplary embodiments disclosed herein are only for illustrative purposes and should not be construed as limiting the scope of the present application. The scope of the present application is therefore indicated by the appended claims rather than by the foregoing description. All changes which come within the meaning and range of equivalency of the claims are to be embraced within the scope of the present application.

What is claimed is:

1. Uridine diphosphate (UDP)-glycosyltransferase B (UGT-B) comprising the amino acid sequence of SEQ ID NO: 1.

2. A microorganism comprising uridine diphosphate (UDP)-glycosyltransferase B (UGT-B) according to claim 1 or a polynucleotide encoding the uridine diphosphate (UDP)-glycosyltransferase B (UGT-B).

3. A method for producing rebaudioside D, the method comprising reacting nucleotide diphosphate to which glucose is bonded with rebaudioside A in the presence of uridine diphosphate (UDP)-glycosyltransferase B (UGT-B) according to claim 1 to prepare rebaudioside D.

4. The method of claim 3, wherein the nucleotide diphosphate to which glucose is bonded is prepared by reacting sucrose and nucleotide diphosphate in the presence of a sucrose synthase.

5. The method of claim 3, wherein the rebaudioside A is prepared by reacting nucleotide diphosphate to which glucose is bonded with stevioside in the presence of uridine diphosphate (UDP)-glycosyltransferase A (UGT-A).

6. The method of claim 4, wherein the sucrose synthase is a protein consisting of an amino acid sequence of SEQ ID NO: 3.

7. The method of claim 5, wherein the uridine diphosphate (UDP)-glycosyltransferase A (UGT-A) is a protein consisting of an amino acid sequence of SEQ ID NO: 2.

8. The method of claim 3, wherein the method is performed consecutively in situ.

9. A method for producing rebaudioside M, comprising:
reacting nucleotide diphosphate to which glucose is bonded with rebaudioside A in the presence of uridine diphosphate (UDP)-glycosyltransferase B (UGT-B) according to claim 1 to prepare rebaudioside D; and
reacting the rebaudioside D with nucleotide diphosphate to which glucose is bonded in the presence of uridine diphosphate (UDP)-glycosyltransferase A (UGT-A) to prepare rebaudioside M.

10. The method of claim 9, wherein the uridine diphosphate (UDP)-glycosyltransferase A (UGT-A) is a protein consisting of an amino acid sequence of SEQ ID NO: 2.

11. The method of claim 9, wherein the nucleotide diphosphate to which glucose is bonded is prepared by reacting sucrose with nucleotide diphosphate in the presence of a sucrose synthase.

12. The method of claim 9, wherein the rebaudioside A is prepared by reacting nucleotide diphosphate to which glucose is bonded with stevioside in the presence of uridine diphosphate (UDP)-glycosyltransferase A (UGT-A).

13. The method of claim 11, wherein the sucrose synthase is a protein consisting of an amino acid sequence of SEQ ID NO: 3.

14. The method of claim 12, wherein the uridine diphosphate (UDP)-glycosyltransferase A (UGT-A) is a protein consisting of an amino acid sequence of SEQ ID NO: 2.

15. The method of claim 9, wherein the method is performed consecutively in situ.

* * * * *